(12) United States Patent
Koumura

(10) Patent No.: US 8,144,992 B2
(45) Date of Patent: Mar. 27, 2012

(54) EYE CONDITION DETECTION APPARATUS AND METHOD FOR INSTALLING SAME

(75) Inventor: Takashi Koumura, Toyota (JP)

(73) Assignee: Denso Corporation, Kariya (JP)

( * ) Notice: Subject to any disclaimer, the term of this patent is extended or adjusted under 35 U.S.C. 154(b) by 1203 days.

(21) Appl. No.: 11/902,668

(22) Filed: Sep. 25, 2007

(65) Prior Publication Data

US 2008/0089559 A1  Apr. 17, 2008

(30) Foreign Application Priority Data

Oct. 11, 2006  (JP) ................................. 2006-277304

(51) Int. Cl.
 *G06K 9/46* (2006.01)
(52) U.S. Cl. ....................................................... 382/190
(58) Field of Classification Search .................. None
 See application file for complete search history.

(56) References Cited

U.S. PATENT DOCUMENTS

| | | | |
|---|---|---|---|
| 5,801,763 A | 9/1998 | Suzuki | |
| 6,952,498 B2 | 10/2005 | Ishikura | |
| 2006/0087582 A1 | 4/2006 | Scharenbroch et al. | |
| 2007/0115099 A1 | 5/2007 | Hamada | |

FOREIGN PATENT DOCUMENTS

| | | |
|---|---|---|
| CN | 1830389 | 9/2006 |
| EP | 1655687 A2 * | 5/2006 |
| JP | A-H07-191384 | 7/1995 |
| JP | A-2003-308523 | 10/2003 |
| JP | A-2005-081101 | 3/2005 |
| JP | A-2005-242428 | 9/2005 |
| JP | A-2005-266868 | 9/2005 |
| JP | A-2005-296383 | 10/2005 |
| JP | A-2005-323180 | 11/2005 |

OTHER PUBLICATIONS

Second Office Action dated Apr. 7, 2010 from the China Patent Office in the corresponding CN application No. 200710180139.9 (and English Translation).

(Continued)

*Primary Examiner* — Daniel Mariam
*Assistant Examiner* — Elisa Rice
(74) *Attorney, Agent, or Firm* — Posz Law Group, PLC

(57) ABSTRACT

A driver's eye condition detection is conducted by an eye condition detection apparatus including a right/left near-infrared light sources, a camera and an ECU installed therein. The right side near-infrared light source is positioned on a right side relative to the camera in a driver's view, and a light axis of the right side near-infrared light source is tilted to the right by 15 to 45 degrees relative to an imaging direction of the camera. Further, the left side near-infrared light source is positioned on a left side relative to the camera in a driver's view, and a light axis of the right side near-infrared light source is tilted to the left by 15 to 45 degrees relative to an imaging direction of the camera. In this manner, detection errors of the driver's eye condition are reduced.

25 Claims, 6 Drawing Sheets

OTHER PUBLICATIONS

Office Action dated Jun. 5, 2009 from the China Patent Office in the corresponding CN application No. 2007101801399 (and English Translation).

Office Action dated Nov. 2, 2010 from the China Patent Office in corresponding CN application No. 200710180139.9 (and English Translation).

Office Action mailed Jul. 6, 2011 in corresponding CN application No. 200710180139.9 (and English translation).

Office Action mailed on Jun. 14, 2011 in the corresponding Japanese patent application No. 2006-277304 (English translation enclosed).

* cited by examiner

FIG. 4
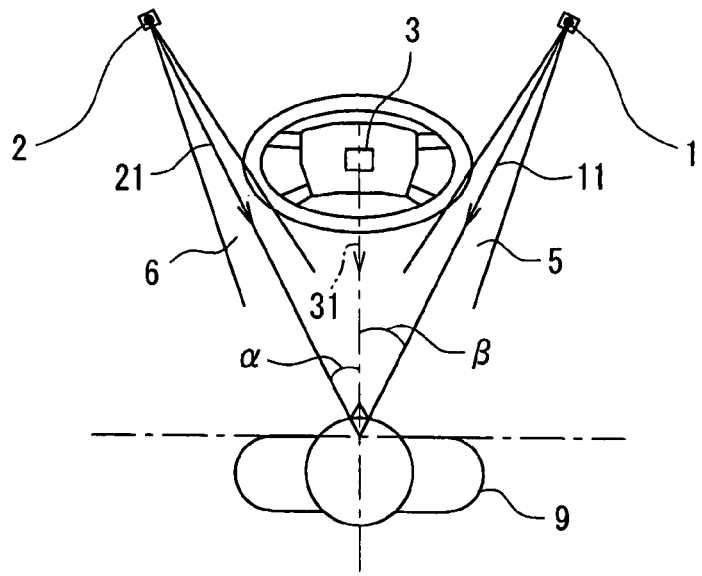
FIG. 5     FIG. 6     FIG. 7
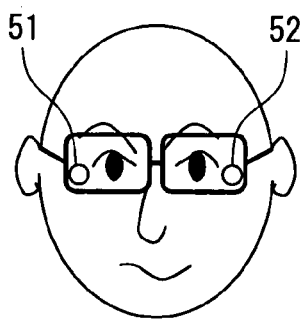 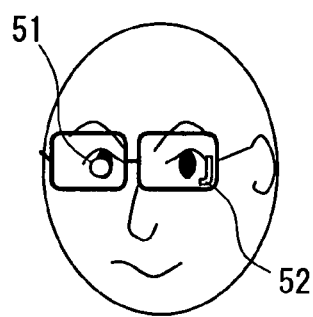 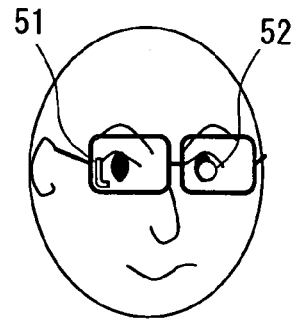
FIG. 10    FIG. 11    FIG. 12
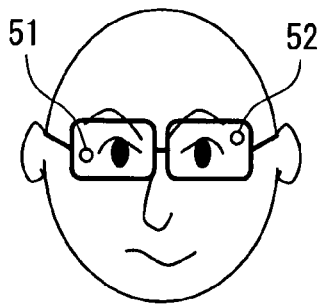 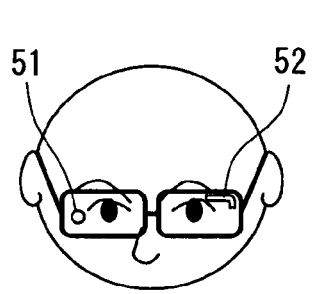 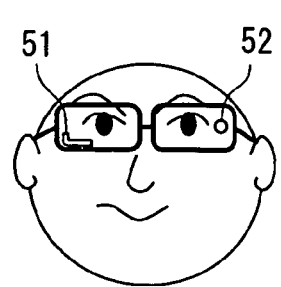

FIG. 13
| NO. OF TESTEE | 148 |
|---|---|
| NO. OF UNDETECTABLE | 2 |
| UNDETECTABLE RATE | 1.4% |
FIG. 14
| NO. OF TESTEE | 86 |
|---|---|
| NO. OF UNDETECTABLE | 18 |
| UNDETECTABLE RATE | 20.9% |
FIG. 15
PRIOR ART
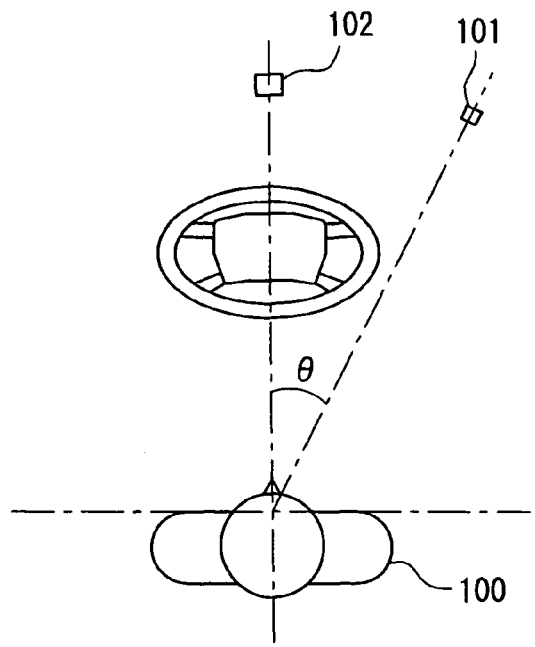
FIG. 16
PRIOR ART
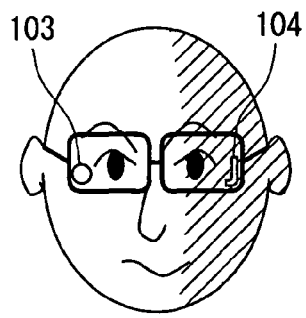
FIG. 17
PRIOR ART
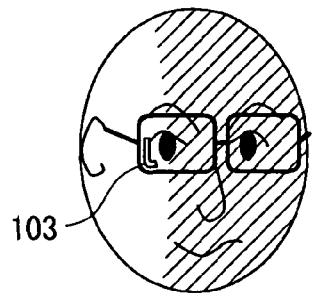
FIG. 18
PRIOR ART
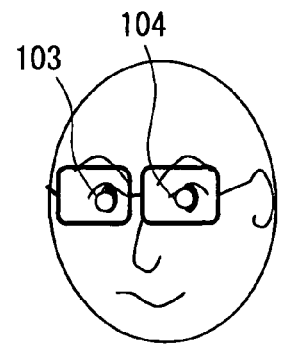

EYE CONDITION DETECTION APPARATUS AND METHOD FOR INSTALLING SAME

CROSS REFERENCE TO RELATED APPLICATION

This application is based on and claims the benefit of priority of Japanese Patent Application No. 2006-277304 filed on Oct. 11, 2006, the disclosure of which is incorporated herein by reference.

FIELD OF THE DISCLOSURE

The present disclosure generally relates to a driver's eye condition detection apparatus and a method for installing a driver's eye condition detection apparatus.

BACKGROUND INFORMATION

There have been conventionally proposed eye condition detection apparatus for detecting the eye condition (e.g., blinking and gaze direction) of a vehicle driver. For example, the eye condition detection apparatus disclosed in Patent Document 1 (i.e., Japanese Patent Document JP-A-H09-21611, also published as U.S. Pat. No. 5,801,763) includes: a light source for illuminating a driver's face; a camera for shooting the illuminated driver's face from the front; and an image processing unit that detects the eye condition from the image of the face picked up by the camera.

Patent Document 1 further discloses that: the light source is disposed in a position away from the camera upward, downward, leftward, or rightward; at this time, the angle formed between the direction of the optical axis of the light source and the shooting direction of the camera is set to approximately 20° to 30° or more. This disposition is for preventing the following from taking place: light projected from the light source is reflected by the lens of a driver's eyeglasses and the reflected light enters the image pickup lens of the camera.

In the Patent Document 1, the present inventors paid attention to that there was only one installation position of the light source for preventing reflected light from an eyeglass lens from entering the image pickup lens of the camera. The present inventors found that in this case, a problem would arise by investigation and experiment.

To explain this problem, FIG. 15 illustrates an example where the direction of the optical axis of a light source 101 is shifted rightward from the shooting direction of a camera 102 (i.e., the direction of the optical axis of a lens of the camera 102). In this case, the direction of the optical axis of the light source 101 is a direction extending from the light source 101 to the estimated position of the head of a driver 100 when he/she sits on the driver's seat. The shooting direction is a direction extending from the camera 102 to the estimated position.

FIG. 16 to FIG. 18 illustrate picked up images of the driver 100's face generated by the camera 102 in this case.

FIG. 16 is an image picked up when the driver 100's face is facing right in front relative to the camera 102. In this case, the side of the face farther from the light source 101 is shaded, and this makes the shaded portion in the image dark. Therefore, it is difficult for the image processing unit to detect the eye on the shaded side. To reduce the influences 103, 104 of the reflection of light from the light source 101 by an eyeglass lens, it is effective to increase the angle formed between the direction of the optical axis of the light source 101 and the shooting direction of the camera 102. However, as the angle formed between the two directions is increased, the above-mentioned adverse effect of shade becomes more noticeable.

FIG. 17 is an image picked up when the driver 100's face is facing toward the side where there is no light source 101 for the camera 102, that is, the face is facing toward the left of the driver 100. In this case, most of the surface of the face is not illuminated with light from the light source and is shaded, and the entire face in the image is darkened. Therefore, it is extremely difficult for the image processing unit to detect an eye.

FIG. 18 is an image picked up by the camera 102 when the driver 100's face is facing toward a direction between the light source 101 and the camera 102. In this case, light is reflected by both the eyeglass lenses, and the reflections 103, 104 are superposed on the eyes. As a result, the image processing unit cannot detect either eye.

In the above example, the direction of the optical axis of a light source is just shifted leftward or rightward from the optical axis of a camera. In this case, it is difficult to detect an eye in almost all the directions in which the driver's face faces. In many periods of time for which the driver is driving a vehicle, it is difficult to carry out the detection of an eye that is an intended purpose of the related art.

FIG. 19 illustrates an example where the direction of the optical axis of a light source 101 is shifted only upward from the shooting direction of a camera 102. That is, the drawing illustrates an example where the light source 101 is disposed away from the camera 102 under the cameral in the vertical direction.

FIG. 20 and FIG. 21 respectively illustrate images picked up by the camera 102 when the driver 100's face in the example of FIG. 19 is facing in the horizontal direction and upward. In these cases, bright spots 103, 104 produced as the result of reflection by eyeglass lenses are shifted from the positions of eyes.

According to the investigation and experiment conducted by the present inventors, however, the following problem arises in the example illustrated in FIG. 19:

FIG. 22 illustrates an image picked up by the camera 102 when the driver 100's face in the example of FIG. 19 is facing in a direction lower than the light source 101. FIG. 23 illustrates an image picked up by the camera 102 when the driver 100's face in the example of FIG. 19 is facing in a direction between the light source 101 and the camera 102. When a face is slightly drooped or turned slightly downward as in these examples, bright spots 103, 104 superposed on both of the eyeglass lenses are produced, and neither of the eyes can be detected. These orientations of a face quite often occur when a driver drives a vehicle or operates equipment in the vehicle compartment. Therefore, in a certain period of time for which the driver is driving the vehicle, neither of his/her eyes can be detected.

A driver 100 often wears his/her eyeglasses in a slightly lower position as illustrated in FIG. 24. In this case, a problem arises even though the optical axis of the light source 101 and the shooting direction of the camera 102 are separated from each other in the vertical direction. When the driver 100 turns his/her face in the horizontal direction as illustrated in FIG. 25, bright spots are produced by reflection by the eyeglass lenses.

As mentioned above, it is difficult to detect an eye in almost all the orientations of the face just by shifting the direction of the optical axis of a light source from the optical axis of a camera in the vertical direction. In many periods of time for which a driver is driving a vehicle, it is difficult to carry out the detection of an eye that is an intended purpose of the related art.

SUMMARY OF THE DISCLOSURE

In consideration of the foregoing, it is an object of the invention to devise the disposition of a light source with respect to the techniques associated with an eye condition detection apparatus for detecting the eye condition of a vehicle driver, and thereby reduce the frequency of occurrence of a situation in which an eye cannot be detected as compared with conventional cases.

According to a first aspect of the invention to attain the above object, an eye condition detection apparatus includes: a first light source (1); a second light source (2); a camera (3) for shooting the eyes of a vehicle driver illuminated by the first light source (1) and the second light source (2); and a control unit (4) that carries out control based on the state of the eyes shot by the camera (3). In this eye condition detection apparatus, the first light source (1) is disposed on the right of the camera (3) as viewed from the driver's seat. At the same time, the direction of the optical axis (11) of the first light source (1) is angled rightward from the shooting direction (31) of the camera (3). The second light source (2) is disposed on the left of the camera (3) as viewed from the driver's seat. At the same time, the direction of the optical axis (21) of the second light source (2) is angled leftward from the shooting direction (31) of the camera (3). The shooting direction of the camera cited here refers to a direction extending from the camera to the center of an area to be shot. The direction of the optical axis of a light source refers to a direction extending from the light source to the center of an object to be illuminated.

As mentioned above, the first light source and the second light source are respectively disposed on the left and right of the camera. In addition, the directions of the optical axes of the first light source and the second light source are respectively angled rightward and leftward from the shooting direction of the camera. Therefore, the driver's face is illuminated with light from both sides. As a result, the possibility that the face is shaded is reduced.

According to the result of the experiment conducted by the present inventors, the following takes place in this case: when the driver's face is facing toward the front of the camera, bright spots, if produced on the eyeglass lenses by the first and second light sources, are often positioned close to the left and right ends of the eyeglass lenses. (Refer to FIG. 5.) Therefore, the possibility that bright spots are superposed on the outlines of both eyes is reduced.

Further, the result of the experiment conducted by the present inventors reveals the following: when the face is facing to the right, a bright spot superposed on the outline of the right eye may be produced on the right eyeglass lens. However, a bright spot superposed on the outline of the left eye is rarely produced on the left eyeglass lens. (Refer to FIG. 6.)

Further, the result of the experiment conducted by the present inventors reveals the following: when the face is facing to the left, a bright spot superposed on the outline of the left eye may be produced on the left eyeglass lens. However, a bright spot superposed on the outline of the right eye is rarely produced on the right eyeglass lens. (Refer to FIG. 7.)

As mentioned above, multiple light sources are prepared. The light sources are disposed on the left and right of a camera, and the directions of their optical axes are angled from the shooting direction of the camera. Thus, with respect to the techniques associated with eye condition detection apparatus for detecting the eye condition of a vehicle driver, the frequency of occurrence of a situation in which an eye cannot be detected is reduced.

That the light sources are disposed on the right side and the left side includes not only cases where they are disposed on the right and left of a camera in the horizontal direction. It also includes cases where they are disposed on the right and left of the camera in an oblique direction.

At this time, the direction of the optical axis (11) of the first light source (1) is angled rightward by 15° or more from the shooting direction (31) of the camera (3). The direction of the optical axis (21) of the second light source (2) is angled leftward by 15° or more from the shooting direction (31) of the camera (3).

According to the result of the experiment conducted by the present inventors, in these cases, the following can be implemented with respect to the techniques associated with eye condition detection apparatus for detecting the eye condition of a vehicle driver: the frequency of occurrence of a situation in which an eye cannot be detected is substantially zeroed substantially regardless of the type of eyeglasses and the way eyeglasses are worn.

The positions of the light sources and the camera are variously modified as long as the driver's face is not shaded. That is, for example, the first and second light sources may be positioned horizontally away (rightward/leftward) from a straight front direction of the camera, or vertically away (upward/downward). The positions of the first and the second light sources may be defined by an angle from the straight front direction of the camera, by a distance on a dashboard of the vehicle or the like. The position may be defined relative to a position of the driver's head, and the position of the driver's head may be defined based on a position of a driver's seat with its slidable adjustment margin in a longitudinal direction of the vehicle and with a pivotal adjustment margin of the backrest. Further, the positions of the light sources and the camera may be defined relative to various parts such as a steering column, a pillar, a rearview mirror or the like in the vehicle. In addition, the eye condition detection apparatus may be used in a large commercial vehicle, and the positions of the light sources and the camera may be symmetrically switched when the vehicle or the large commercial vehicle is designed for left hand traffic instead of right hand traffic (i.e., a handle position is on the left side in the vehicle instead of on the right side).

The first aspect of the invention can also be grasped as a method for installing an eye condition detection apparatus characterized in that: the first light source (1) is disposed on the right of the camera (3) as viewed from the driver's seat; the direction of the optical axis (11) of the first light source (1) is angled rightward from the shooting direction (31) of the camera (3); the second light source (2) is disposed on the left of the camera (3) as viewed from the driver's seat; and the direction of the optical axis (21) of the second light source (2) is angled leftward from the shooting direction (31) of the camera (3).

Further, the variations of the light source positions and the camera positions may also be described as the methods of installation of those parts in the vehicle.

BRIEF DESCRIPTION OF THE DRAWINGS

Other objects, features and advantages of the present invention will become more apparent from the following detailed description made with reference to the accompanying drawings, in which:

FIG. 4 shows a top view of near-infrared illumination lamp light axes and a camera direction in the vehicle;

FIG. 5 shows an illustration of a driver's face image when a driver is facing straight toward the camera;

FIG. 6 shows an illustration of a driver's face image when the driver is facing rightward from the camera;

FIG. 7 shows an illustration of a driver's face image when the driver is facing leftward from the camera;

FIG. 10 shows an illustration of a driver's face image when the driver is facing in a level direction;

FIG. 11 shows an illustration of a driver's face image when the driver is facing in a downward direction;

FIG. 12 shows an illustration of a driver's face image when the driver is facing in an upward direction;

FIG. 13 shows a diagram of experiment results regarding a blink detection experiment in the second embodiment;

FIG. 14 shows a diagram of experiment results regarding a blink detection experiment in another embodiment;

FIG. 15 shows an illustration of a rightward shift of a light axis of a light source relative to an imaging direction of the camera;

FIG. 16 shows an illustration of a driver's face image when the driver is facing straight to the camera;

FIG. 17 shows an illustration of a driver's face image when the driver is facing leftward from the camera;

FIG. 18 shows an illustration of a driver's face image when the driver is facing in a direction between the light source and the camera;

DETAILED DESCRIPTION

Embodiments of the present disclosure are described with reference to the accompanying drawings. Though the descriptions in the following embodiments are aimed at a situation in the vehicle wherein a steering wheel is disposed on a right side in a vehicle body, the disclosure of the invention may be applied to the vehicle wherein a steering wheel is disposed on a left side in a vehicle body if right-left relationships are switched.

First Embodiment

Figure 1:
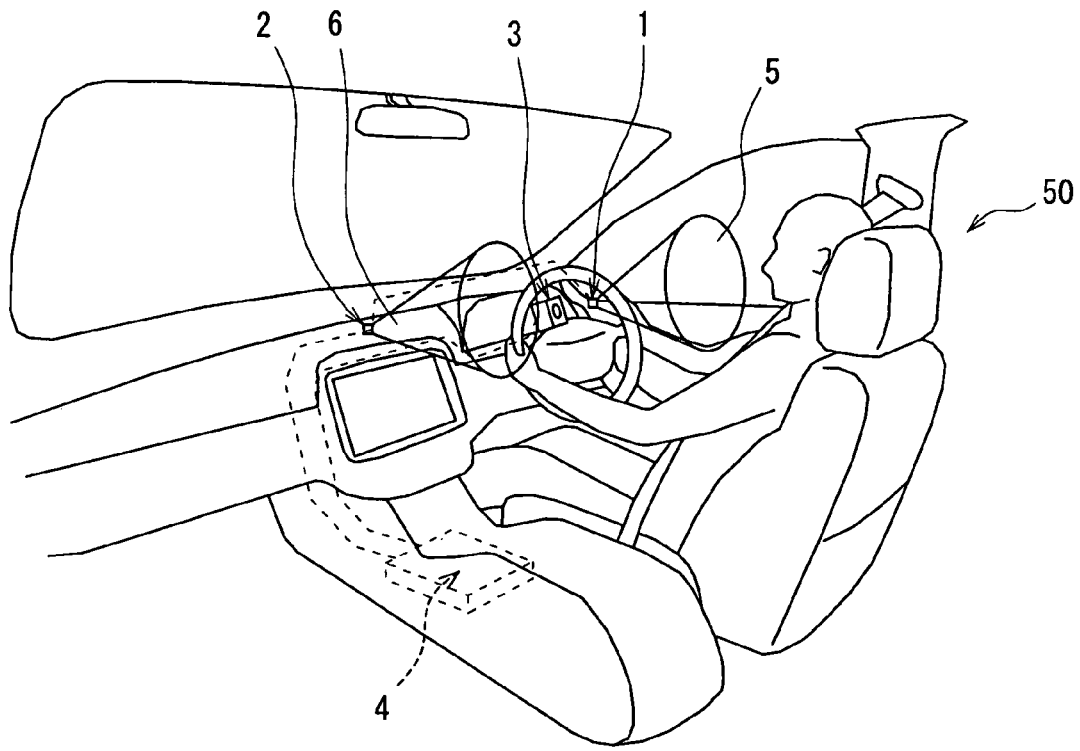
FIG. 1 shows a perspective view of an installation condition of an eye condition detection apparatus in a first embodiment of the present disclosure.

Hereafter, a description will be given to a first embodiment of the invention. FIG. 1 schematically illustrates how an eye condition detection apparatus 50 in this embodiment is installed in a vehicle compartment. The eye condition detection apparatus 50 includes a right near-infrared illumination light source 1, a left near-infrared illumination light source 2, a camera 3, and an ECU 4.

The right near-infrared illumination light source 1 and the left near-infrared illumination light source 2 are light sources, such as LEDs, installed in front of the driver's seat in the vehicle compartment. They are respectively configured to project near-infrared light beams having a spread, shown as light cones 5 and 6, to the head of a driver seated on the driver's seat. Turn-on/off of the right near-infrared illumination light source 1 and the left near-infrared illumination light source 2 is controlled according to signals from the ECU 4.

The camera 3 performs the following operation under the control of the ECU 4: it shoots the face of the driver seated on the driver's seat and outputs to the ECU 4 a signal indicating the picked up image of the face generated as the result of shooting.

The ECU 4 is installed in an inconspicuous area such as the interior of a dashboard on the driver's seat side in the vehicle compartment. The ECU controls the right near-infrared illumination light source 1, left near-infrared illumination light source 2, and camera 3, and acquires picked up images from the camera 3.

Figure 2:
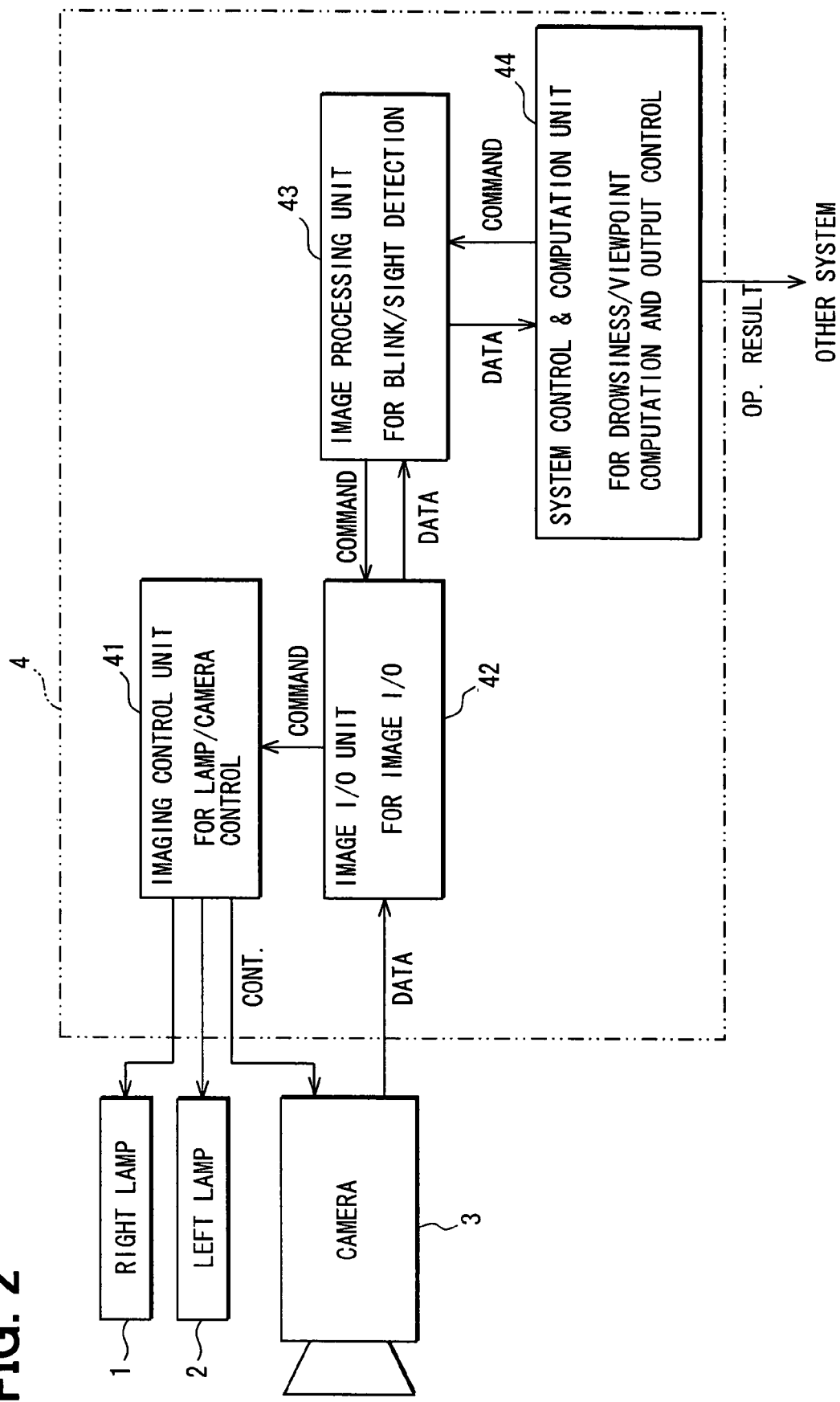
FIG. 2 shows a block diagram of a right/left near-infrared illumination lamp, a camera and an ECU with electrical connections therebetween.

FIG. 2 is a block diagram illustrating the electrical connection among a right near-infrared illumination light source 1, a left near-infrared illumination light source 2, a camera 3, and an ECU 4 and the configuration of the ECU 4. As illustrated in this drawing, the ECU 4 includes an imaging control unit 41, an image input/output unit 42, an image processing unit 43, and a system control and computation unit 44. These components 41 to 44 of the ECU 4 may be constructed of, for example, a publicly known microcomputer.

The system control and computation unit 44 outputs a shooting request command to the image processing unit 43 whenever a shooting time comes (e.g., periodically). The image processing unit 43 outputs the shooting request command received from the system control and computation unit 44 to the image input/output unit 42. The image input/output unit 42 outputs the shooting request command received from the image processing unit 43 to the imaging control unit 41. In response to the reception of the shooting request command from the image input/output unit 42, the imaging control unit 41 controls the camera 3 and causes the camera 3 to shoot the driver's face. (This corresponds to camera shooting control function.)

The camera 3 generates and outputs a picked up image under the control of the imaging control unit 41. Then, the image input/output unit 42 receives the picked up image outputted from the camera 3. (This corresponds to camera image input function.) Further, the image input/output unit 42 outputs a signal of the received image to the image processing unit 43. (This corresponds to camera output function.) Based on the signal of the picked up image received from the image input/output unit 42, the image processing unit 43 identifies the outline of an eye, the position of a pupil, and the like in the picked up image using a publicly known image processing technique. Then, it detects the direction of the driver's line of sight based on the relative position of the pupil inside the outline of the eye. (This corresponds to line of sight detecting function.) Further, based on the presence or absence of a pupil in the picked up image from the image input/output unit 42 or the like, the image processing unit 43 determines whether or not the driver is blinking. (This corresponds to a blink detecting function.) Then, the image processing unit 43 outputs to the system control and computation unit 44 detection data related to the direction of the driver's line of sight and the presence or absence of blinking.

When the system control and computation unit 44 receives the detection data related to the direction of the driver's line of sight and the presence or absence of blinking from the image processing unit 43, it performs the following processing: it identifies where the driver is regarding based on the data (This corresponds to a point-of-regard computation function.); and it presumes whether or not the driver is drowsy (This corresponds to a drowsiness presuming computation function.) The system control and computation unit 44 outputs the information of the point of regard and the presence or absence of drowsiness, obtained as the result of processing, to other systems in the vehicle. (This corresponds to computation result output control function.)

A system that received the information of the point of regard carries out control to, for example, aim the direction of the optical axis of a headlight toward the direction of the point of regard. A system that received the information of the presence of drowsiness carries out control to, for example, causes a speaker to sound an alert.

The system control and computation unit 44 outputs an illuminate light command to the image processing unit 43 when necessary, for example, in the nighttime. The image processing unit 43 outputs the illuminate light command received from the system control and computation unit 44 to the image input/output unit 42. The image input/output unit 42 outputs the illuminate light command received from the image processing unit 43 to the imaging control unit 41. In response to the reception of the illuminate light command from the image input/output unit 42, the imaging control unit 41 turns on the right near-infrared illumination light source 1 and the left near-infrared illumination light source 2.

As the result of the above operation, the driver's face is illuminated. Thus, the camera 3 can shoot the driver's face illuminated with light from the right near-infrared illumination light source 1 and the left near-infrared illumination light source 2. The ECU 4 can identify the state of eyes from the thus obtained picked-up image through image processing.

Figure 3:
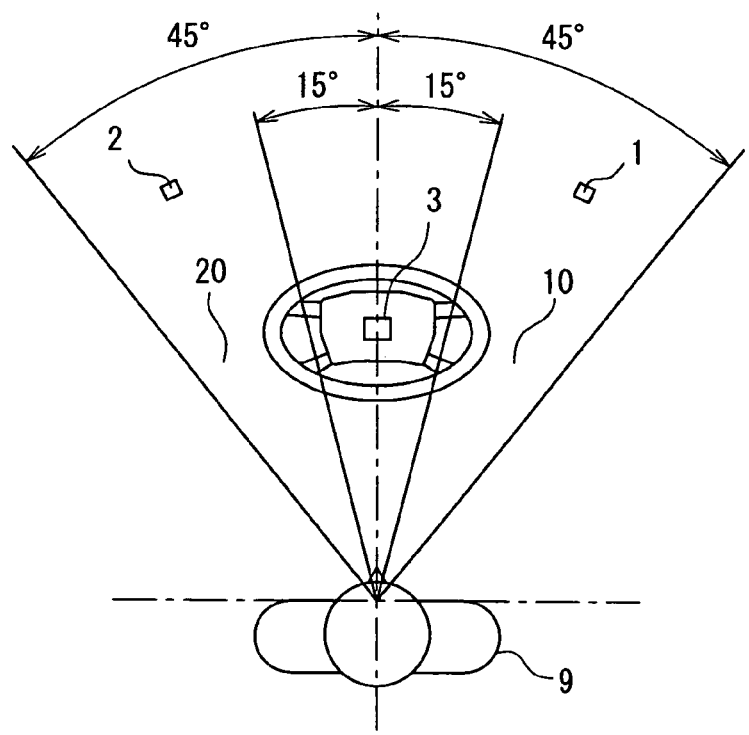
FIG. 3 shows a top view of near-infrared illumination lamp positions and a camera position in a vehicle.

A description will be given to the disposition of the right near-infrared illumination light source 1, left near-infrared illumination light source 2, and camera 3 in the vehicle compartment. FIG. 3 is a schematic view of the interior of the vehicle compartment as viewed from above. The right near-infrared illumination light source 1, left near-infrared illumination light source 2, and camera 3 are installed in the same plane. As illustrated in the drawing, the camera 3 is installed in the center of rotation of a steering wheel positioned in front of the driver 9 seated on the driver's seat. Instead, the camera 3 may be installed in an instrument section that forms the front end of the interior of the vehicle compartment and is positioned in front of the driver. (This front end is the forward facing portion of the ends of the interior of the vehicle compartment.)

Here, it is assumed that the seating portion (i.e., the portion on which the driver's buttocks and femoral regions are placed) of the driver's seat is situated in the following position: a position at equal distances from a position in which the seat is situated when it is moved forward to the limit and a position in which the seat is situated when it is moved backward to the limit. Further, it is assumed that the backrest of the driver's seat is raised perpendicularly to the seating portion.

The right near-infrared illumination light source 1 is installed in the following position with the driver 9's head in the center: a position within an angular range 10 of not less than 15° and not more than 45° to the right from the direction of the front of the driver's seat (i.e. the direction extending from the driver 9's head to the camera 3). Specifically, it is installed at the front end of the right front door. When the right near-infrared illumination light source 1 is installed at the front end of the interior of the vehicle compartment, the distance between the right near-infrared illumination light source 1 and the camera 3 in the direction of the width of the vehicle is not less than 20 centimeters. It is assumed that the driver's head is positioned 10 centimeters directly above the backrest of the driver's seat.

The left near-infrared illumination light source 2 is installed in the following position with the driver 9's head in the center: a position within an angular range 20 of not less than 15° and not more than 45° to the left from the direction of the front of the driver's seat. Specifically, it is installed on an enclosure in proximity to the center of the dashboard of the vehicle from the viewpoint of preventing the driver's view through the windshield from being interrupted. When the left near-infrared illumination light source 2 is installed at the front end of the interior of the vehicle compartment, the distance between the left near-infrared illumination light source 2 and the camera 3 in the direction of the width of the vehicle is not less than 20 centimeters.

The directions of the optical axes of the right near-infrared illumination light source 1 and the left near-infrared illumination light source 2 and the shooting direction of the camera 3 are as illustrated in FIG. 4. The shooting direction 31 of the camera 3 is a direction extending from the camera 3 to the head of the driver 9, that is, a direction extending from the camera 3 to the rear of the vehicle. The shooting direction of the camera 3 cited here refers to a direction that is parallel with the optical axis of the main lens used by the camera 3 for shooting and is directed from the camera 3 to an object of shooting.

The direction of the optical axis 11 of the right near-infrared illumination light source 1 is a direction extending from the right near-infrared illumination light source 1 to the driver 9's head. That is, the direction that is parallel with the central axis of the light cone projected from the right near-infrared illumination light source 1 and is directed from the right near-infrared illumination light source 1 to an object to be illuminated is the above direction. As mentioned above, the right near-infrared illumination light source 1 is installed in a position within an angular range 10 of not less than 15° and not more than 45° to the right from the direction of the front of the driver's seat with the driver 9's head in the center. Therefore, the direction of the optical axis 11 of the right near-infrared illumination light source 1 is angled rightward from the shooting direction of the camera 3 within a range of $\beta=15°$ to 45°.

The direction of the optical axis 21 of the left near-infrared illumination light source 2 is a direction extending from the left near-infrared illumination light source 2 to the driver 9's head. That is, the direction that is parallel with the central axis of the light cone projected from the left near-infrared illumination light source 2 and is directed from the left near-infrared illumination light source 2 to an object to be illuminated is the above direction. As mentioned above, the left near-infrared illumination light source 2 is installed in a position within an angular range 20 of not less than 15° and not more than 45° to the left from the direction of the front of the driver's seat with the driver 9's head in the center. Therefore, the direction of the optical axis 21 of the right near-infrared illumination light source 2 is angled leftward from the shooting direction of the camera 3 within a range of α=15° to 45°.

As mentioned above, the eye condition detection apparatus 50 includes: the right near-infrared illumination light source 1; the left near-infrared illumination light source 2; the camera 3 for shooting the eyes of the vehicle driver illuminated by the right near-infrared illumination light source 1 and the left near-infrared illumination light source 2; and the ECU 4 that carries out control based on the state of the eyes shot by the camera 3. The right near-infrared illumination light source 1 is disposed on the right of the camera 3 as viewed from the driver's seat, 20 centimeters or more away from the camera 3. The optical axis 11 of the right near-infrared illumination light source 1 is angled rightward by 15° to 45° from the shooting direction 31 of the camera 3. The left near-infrared illumination light source 2 is disposed on the left of the camera 3 as viewed from the driver's seat, 20 centimeters or more away from the camera 3. The optical axis 21 of the left near-infrared illumination light source 2 is angled leftward by 15° to 45° from the shooting direction 31 of the camera 3. The eye condition detection apparatus 50 is installed under this setup in the vehicle compartment.

As mentioned above, the first light source and the second light source are respectively disposed on the right and left of the camera. The directions of the optical axes of the first light source and the second light source are respectively angled rightward and leftward from the shooting direction of the camera. Therefore, the driver's face is illuminated with light from both sides of the face. As a result, the possibility that the face is shaded is reduced.

According to the result of the experiment and investigation conducted by the present inventors, in this case, the phenomenon illustrated in FIG. 5 occurs when the driver's face is facing toward the front of the camera. Even when a bright spot 51 due to the right near-infrared illumination light source 1 is produced on the right eyeglass lens and a bright spot 52 due to the left near-infrared illumination light source 2 is produced on the left eyeglass lens, these bright spots are usually produced in proximity to the left and right ends of the eyeglass lenses. Therefore, the bright spots are seldom superposed on the outlines of both the eyes at the same time.

According to the result of the experiment and investigation conducted by the present inventors, the phenomenon illustrated in FIG. 6 occurs when the driver's face is facing to the right. A bright spot due to the right near-infrared illumination light source 1, superposed on the outline of the right eye may be produced on the right eyeglass lens. However, a bright spot superposed on the outline of the left eye is rarely produced on the left eyeglass lens.

According to the result of the experiment and investigation conducted by the present inventors, the phenomenon illustrated in FIG. 7 occurs when the driver's face is facing to the left. A bright spot due to the left near-infrared illumination light source 2, superposed on the outline of the left eye may be produced on the left eyeglass lens. However, a bright spot superposed on the outline of the right eye is rarely produced on the right eyeglass lens.

As mentioned above, the following can be implemented with respect to the techniques associated with eye condition detection apparatus for detecting the eye condition of a vehicle driver: the frequency of occurrence of a situation in which an eye cannot be detected is reduced by preparing multiple light sources, disposing these light sources on the left and right of a camera, and angling their optical axes from the shooting direction of the camera.

As mentioned above, the following can be implemented with respect to the techniques associated with eye condition detection apparatus for detecting the eye condition of a vehicle driver: the frequency of occurrence of a situation in which an eye cannot be detected is substantially zeroed substantially regardless of the type of eyeglasses and the way eyeglasses are worn.

In the above description, the ECU 4 carries out control based on the state of an eye shot by the camera 3. Instead, it may be configured to carry out control based on the state of an eye shot by the camera 3 and computation for presuming the driver's condition.

Second Embodiment

Figure 8:
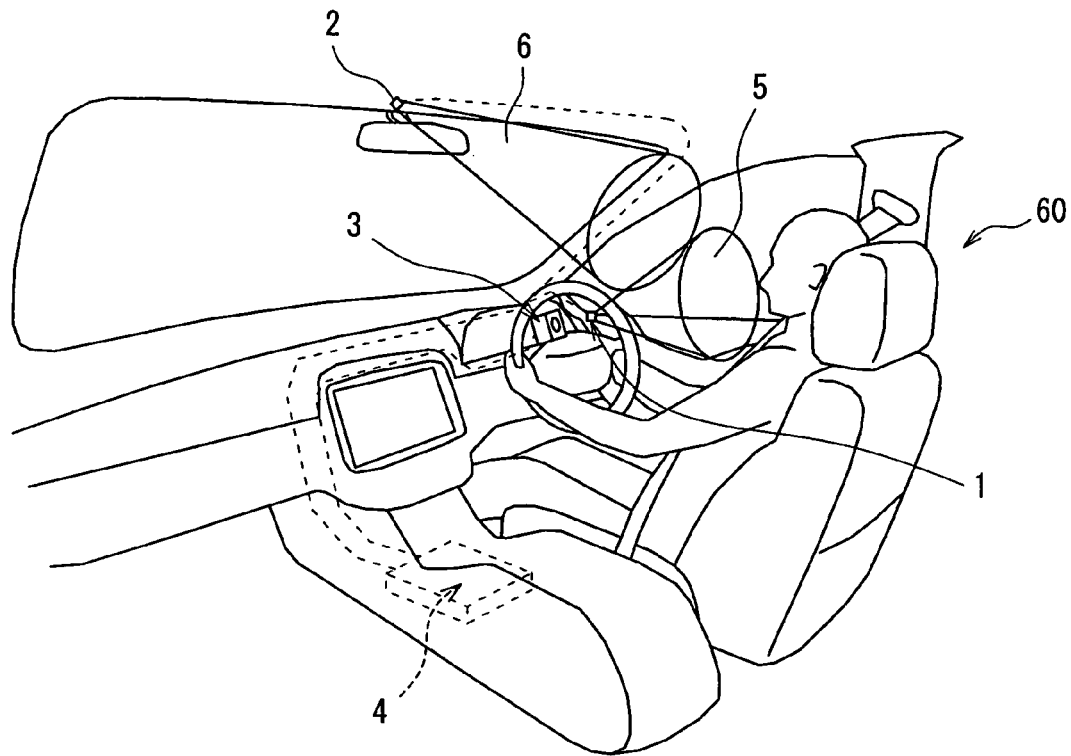
FIG. 8 shows a perspective view of an installation condition of the eye condition detection apparatus in a second embodiment of the present disclosure.

A description will be given to a second embodiment of the invention. FIG. 8 illustrates how an eye condition detection apparatus 60 in this embodiment is installed in a vehicle compartment. The eye condition detection apparatus 60 in this embodiment is different from the eye condition detection apparatus 50 in the first embodiment only in the installation position of the left near-infrared illumination light source 2. However, the installation position of the right near-infrared illumination light source 1 may also be different from that in the first embodiment.

As illustrated in FIG. 8, the left near-infrared illumination light source 2 in this embodiment is installed above the right near-infrared illumination light source 1 and the camera 3. More specifically, the left near-infrared illumination light source 2 is installed on the ceiling of the vehicle compartment in a position corresponding to the base of an inside rearview mirror.

Figure 9:
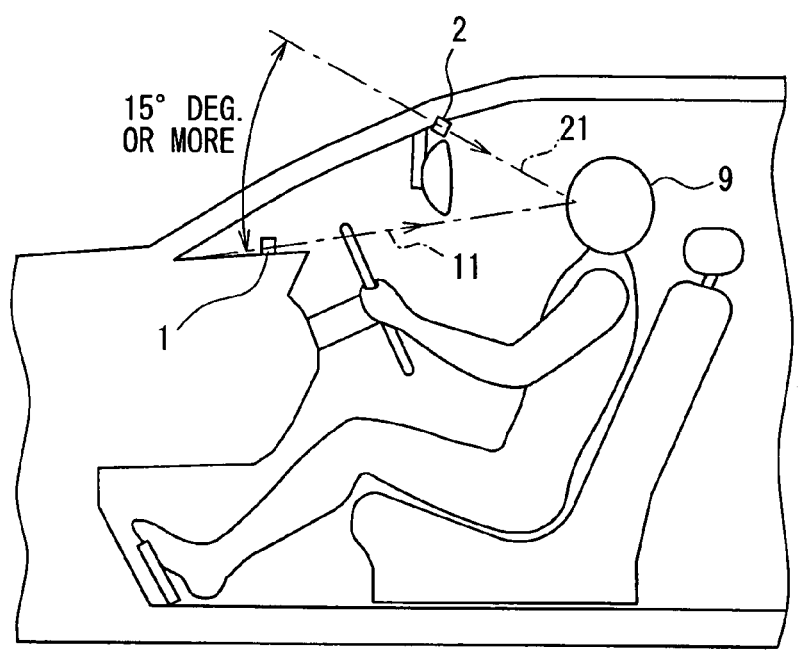
FIG. 9 shows a side view of the near-infrared illumination lamp positions in the vehicle.
Figure 19:
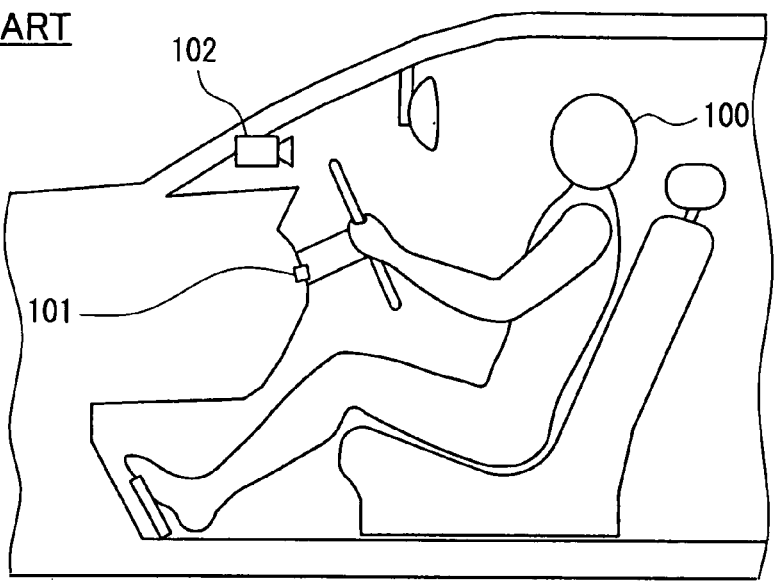
FIG. 19 shows an illustration of an shift of the light axis of the light source exclusively in an upward direction relative to an imaging direction of the camera.
Figure 20:
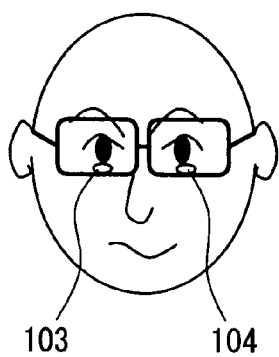
FIG. 20 shows an illustration of a driver's face image captured by the camera when the driver is facing in a level direction.
Figure 21:
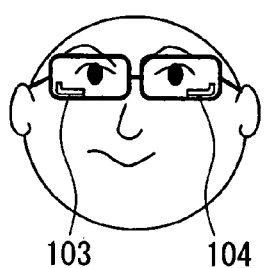
FIG. 21 shows an illustration of a driver's face image captured by the camera when the driver is facing in an upward direction.
Figure 22:
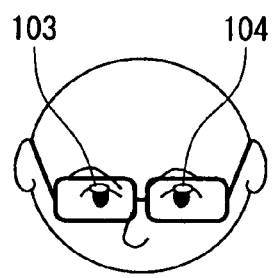
FIG. 22 shows an illustration of a driver's face image captured by the camera when the driver is facing in a downward direction relative to the light source.
Figure 23:
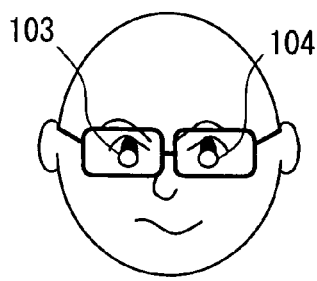
FIG. 23 shows an illustration of a driver's face image captured by the camera when the driver is facing in a direction between the light source and the camera.
Figure 24:
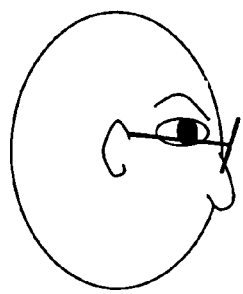
FIG. 24 shows an illustration of a driver's face when the driver wears glasses slightly downwardly.
Figure 25:
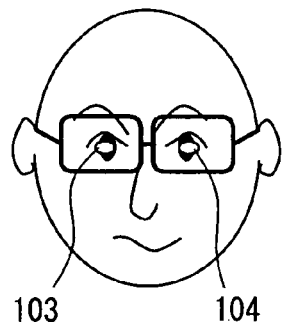
FIG. 25 shows an illustration of a driver's face image by the camera when the driver is facing a level direction in a condition shown in FIG. 24.

FIG. 9 illustrates the interior of the vehicle compartment viewed from a lateral side of the vehicle. As illustrated in this drawing, the optical axis 11 of the right near-infrared illumination light source 1 and the optical axis 21 of the left near-infrared illumination light source 2 are so set that the following implemented: when they are projected onto a plane containing the vertical direction and the direction of the length of the vehicle, the angle formed between the two projected lines is not less than 15°.

As mentioned above, the direction of the optical axis 11 of the right near-infrared illumination light source 1 may be angled by 15° or more from the optical axis 21 of the left near-infrared illumination light source 2 in the vertical direction. With this construction, the following positions are misaligned in the vertical direction: the position of a bright spot produced on the right eyeglass lens by the first light source and the position of a bright spot produced on the left eyeglass lens by the second light source.

Some examples will be taken. When the driver is facing front in the horizontal direction, the phenomenon illustrated in FIG. 10 occurs. That is, the bright spot 52 produced on the left eyeglass lens by the left near-infrared illumination light source 2 is shifted upward as compared with the bright spot 52 illustrated in FIG. 5 associated with the first embodiment. When the driver is facing forward and downward, the phenomenon illustrated in FIG. 11 occurs. While the bright spot 51 still remains in the eyeglass lens, the bright spot 52 is moved to the edge of the eyeglass lens. When the driver is facing forward and upward, the phenomenon illustrated in FIG. 12 occurs. While the bright spot 52 still remains in the eyeglass lens, the bright spot 51 is moved to the edge of the eyeglass lens. Thus, the possibility that bright spots are simultaneously superposed on both eyes is more remarkably reduced.

FIG. 13 is a table showing the result of the experiment on blink detection conducted by the present inventors using the eye condition detection apparatus 60 in the second embodiment. This experiment was conducted under the following conditions. The angular difference between the optical axis 11 of the right near-infrared illumination light source 1 and the shooting direction of the camera 3 projected in the horizontal direction was 19°. The angular difference between the optical axis 11 of the right near-infrared illumination light source 1 and the shooting direction of the camera 3 projected in the vertical direction was 7°. (The right near-infrared illumination light source 1 was positioned at a level lower than the camera 3.) The angular difference between the optical axis 21 of the left near-infrared illumination light source 2 and the shooting direction of the camera 3 projected in the horizontal direction was 17°. The angular difference between the optical axis 21 of the left near-infrared illumination light source 2 and the shooting direction of the camera 3 projected in the vertical direction was 28°. (The right near-infrared illumination light source 1 was positioned at a level higher than the camera 3.) Using the state detection apparatus 60 set up as mentioned above, blink detection processing was carried out on 148 persons with eyeglasses on. Blinking could not be detected only in two persons, which accounted for 1.4 percent.

FIG. 14 is a table showing the result of the experiment on blink detection conducted using an eye condition detection apparatus under conditions to which the invention or the technique disclosed in Patent Document 1 is not applied. This experiment was conducted under the following conditions. The angular difference between the optical axis 11 of the right near-infrared illumination light source 1 and the shooting direction of the camera 3 projected in the horizontal direction was 3°. The angular difference between the optical axis 11 of the right near-infrared illumination light source 1 and the shooting direction of the camera 3 projected in the vertical direction was 0°. The angular difference between the optical axis 21 of the left near-infrared illumination light source 2 and the shooting direction of the camera 3 projected in the horizontal direction was 3°. The angular difference between the optical axis 21 of the left near-infrared illumination light source 2 and the shooting direction of the camera 3 projected in the vertical direction was 0°. Using the eye condition detection apparatus 60 set up as mentioned above, blink detection processing was carried out on 86 persons who wore eyeglasses and was facing substantially front. Blinking could not be detected in 18 persons, which accounted for 20.9 percent.

Other Embodiments

Up to this point, a description has been given to embodiments of the invention. However, the scope of the invention is not limited to the above embodiments, and includes various modes that make it possible to carry out the functions of each feature of the invention.

Although the present invention has been fully described in connection with the preferred embodiment thereof with reference to the accompanying drawings, it is to be noted that various changes and modifications will become apparent to those skilled in the art.

For example, the angle between the light axis of the illumination light sources 1, 2 and the shooting direction of the camera 3 may be less than 15°. In this manner, the advantage of the second embodiment of the present disclosure can substantially be achieved.

Further, the vertical angle between the two illumination light sources 1, 2 may be less than 15°. In this manner, the advantage of the second embodiment of the present disclosure can substantially be achieved.

Furthermore, the positions of the illumination light sources 1, 2 may be varied from the one described in the first and the second embodiment.

For example, the right near-infrared illumination light source 1 may be disposed on a right front pillar, or on a right end of the dashboard structure in the vehicle.

In addition, the left near-infrared illumination light source 2 may be disposed in a proximity of the rearview mirror, an upper end of a center portion of the dashboard.

Furthermore, the number of the illumination light sources may be more than three for lighting the driver's face. In that case, at least two of the three light sources may be used as the first/second light sources for achieving the advantage of the present invention.

Furthermore, the light axes 11, 21 may be in parallel with the shooting direction 31 of the camera 3 as long as the driver's face is sufficiently lit by the light from the light sources 1, 2 and the direction from the driver's face to the light sources 1, 2 and the direction from the driver's face to the camera 3 is sufficiently different.

Though the vehicles (including large commercial vehicles) with its steering wheel disposed on the right side in the vehicle body is described in the above embodiments, the vehicle with its steering wheel disposed on the left side in the vehicle body can be accommodated by the present disclosure by switching the positions of the first and the second light sources. That is, the symmetrical position switching of the two light sources 1, 2 can produce the same advantages as described in the first and the second embodiments.

Such changes and modifications are to be understood as being within the scope of the present invention as defined by the appended claims.

What is claimed is:
1. An eye condition detection apparatus comprising:
a first light source;
a second light source;
a camera that images a driver's eye image in a vehicle under a light from the first and the second light sources; and
a control unit that executes a control based on a condition of the driver's eye image imaged by the camera, wherein
the first light source is positioned to the right relative to the camera in a driver's view from a driver's seat with its light axis tilted to the right relative to an imaging direction of the camera,
the second light source is positioned to the left relative to the camera in the driver's view from a driver's seat with its light axis tilted to the left relative to the imaging direction of the camera,
the light axis of the first light source is tilted in a vertical direction relative to the light axis of the second light source,
the first light source is disposed in the vehicle on a right front pillar, and
the second light source is disposed in the vehicle on a surface of a ceiling of the vehicle at a proximity of a foot of a rearview mirror post.

2. The eye condition detection apparatus of claim 1,
wherein the light axis of the first light source is tilted to the right by at least 15 degrees relative to the imaging direction of the camera, and
the light axis of the second light source is tilted to the left by at least 15 degrees relative to the imaging direction of the camera.

3. The eye condition detection apparatus of claim 1,
wherein the light axis of the first light source is tilted by at least 15 degrees in the vertical direction relative to the light axis of the second light source.

4. The eye condition detection apparatus of claim 1,
wherein a steering wheel is disposed on a right side in a vehicle body.

5. The eye condition detection apparatus of claim 1,
wherein the positional relationship between the first light source and the second light source is changed in a right-left symmetrical manner when a steering wheel is disposed on a left side in a vehicle body.

6. The eye condition detection apparatus of claim 1,
wherein the control unit executes a control based on the driver's eye image imaged by the camera and executes an operation for driver's condition determination.

7. An eye condition detection apparatus comprising:
a first light source;
a second light source;
a camera that images a driver's eye image in a vehicle under a light from the first and the second light sources; and
a control unit that executes a control based on a condition of the driver's eye image imaged by the camera, wherein
the camera is positioned in a front direction relative to a driver's seat,
the first light source is positioned on a right side of the camera relative to the front direction with its light axis tilted to the left relative to the front direction,
the second light source is positioned on a left side of the camera relative to the front direction with its light axis tilted to the right relative to the front direction,
the light axis of the first light source is tilted in a vertical direction relative to the light axis of the second light source,
the first light source is disposed in the vehicle on a right front pillar, and
the second light source is disposed in the vehicle on a surface of a ceiling of the vehicle at a proximity of a foot of a rearview mirror post.

8. The eye condition detection apparatus of claim 7,
wherein the light axis of the first light source is tilted by at least 15 degrees to the left relative to the straight front direction, and
the light axis of the second light source is tilted by at least 15 degrees to the right relative to the straight front direction.

9. An eye condition detection apparatus comprising:
a first light source;
a second light source;
a camera that images a driver's eye image in a vehicle under a light from the first and the second light sources; and
a control unit that executes a control based on a condition of the driver's eye image imaged by the camera, wherein
the camera is positioned in a straight front direction relative to a driver's seat in the vehicle,
the first light source is positioned at a front part of the driver's seat in a front portion of the vehicle with a rightward position shift by at least 20 centimeters from the camera,
the second light source is positioned at the front part of the driver's seat in the front portion of the vehicle with a leftward position shift by at least 20 centimeters from the camera,
the first light source and the second light source are positioned apart from each other by at least 20 centimeters in the vertical direction of the vehicle,
the first light source is disposed in the vehicle on a right front pillar, and
the second light source is disposed in the vehicle on a surface of a ceiling of the vehicle at a proximity of a foot of a rearview mirror post.

10. An eye condition detection apparatus comprising:
a first light source;
a second light source;
a camera that images a driver's eye image in a vehicle under a light from the first and the second light sources; and
a control unit that executes a control based on a condition of the driver's eye image imaged by the camera, wherein
the first light source is positioned on a right side relative to a head of a driver in a driver's seat with a tilt angle of at least 15 degrees relative to a front direction of the driver,
the second light source is positioned on a left side relative to the head of the driver in the driver's seat with a tilt angle of at least 15 degrees relative to the front direction of the driver,
a direction from the head of the driver to the first light source and a direction from the head of the driver to the second light source make an angle of at least 15 degrees in the vertical direction of the vehicle,
the first light source is disposed in the vehicle on a right front pillar, and
the second light source is disposed in the vehicle on a surface of a ceiling of the vehicle at a proximity of a foot of a rearview mirror post.

11. An eye condition detection apparatus comprising:
a first light source;
a second light source;
a camera that images a driver's eye image in a vehicle under a light from the first and the second light sources; and
a control unit that executes a control based on a condition of the driver's eye image imaged by the camera, wherein
the camera is disposed on one of an outside of a steering column case and an inside of a meter panel of the vehicle,
the first light source is disposed in the vehicle on a right front pillar, and
the second light source is disposed in the vehicle on a surface of a ceiling of the vehicle at a proximity of a foot of a rearview mirror post.

12. An eye condition detection apparatus comprising:
a first light source;
a second light source;
a camera that images a driver's eye image in a large commercial vehicle under a light from the first and the second light sources; and
a control unit that executes a control based on a condition of the driver's eye image imaged by the camera, wherein the camera is disposed on one of an outside of a steering column case, an inside of a meter panel and an outside of the dashboard structure in front of the driver of the large commercial vehicle, the first light source is disposed in the large commercial vehicle on a right front pillar, and the second light source is disposed in the large commercial vehicle on a surface of a ceiling of the large commercial vehicle at a proximity of a foot of a rearview mirror post.

13. The eye condition detection apparatus of claim 12, wherein a steering wheel is disposed on a right side in a large commercial vehicle body.

14. The eye condition detection apparatus of claim 12, wherein the positional relationship between the first light source and the second light source is changed in a right-left symmetrical manner when a steering wheel is disposed on a left side in a large commercial vehicle body.

15. An installation method of an eye condition detection apparatus that includes a first light source, a second light source, a camera for imaging a driver's eye image in a vehicle under a light from the first and the second light sources, and a control unit for executing a control based on a condition of the driver's eye image imaged by the camera, the installation method comprising:

positioning the first light source on a right side of the camera in a driver's view from a driver's seat with its light axis tilted to the right relative to an imaging direction of the camera; and positioning the second light source on a left side of the camera in the driver's view from the driver's seat with its light axis tilted to the left relative to the imaging direction of the camera, wherein the light axis of the first light source is tilted in a vertical direction relative to the light axis of the second light source, the first light source is disposed in the vehicle on a right front pillar, and the second light source is disposed in the vehicle on a surface of a ceiling of the vehicle at a proximity of a foot of a rearview mirror post.

16. The installation method of claim 15, wherein a steering wheel is disposed on a right side in a vehicle body.

17. The installation method of claim 15, wherein the positional relationship between the first light source and the second light source is changed in a right-left symmetrical manner when a steering wheel is disposed on a left side in a vehicle body.

18. An installation method of an eye condition detection apparatus that includes a first light source, a second light source, a camera for imaging a driver's eye image in a vehicle under a light from the first and the second light sources, and a control unit for executing a control based on a condition of the driver's eye image imaged by the camera, the installation method comprising:

positioning the camera in a front direction relative to a driver's seat;

positioning the first light source on a right side of the camera relative to the front direction with its light axis tilted to the left relative to the front direction; and positioning the second light source on a left side of the camera relative to the front direction with its light axis tilted to the right relative to the front direction, wherein the light axis of the first light source is tilted in a vertical direction relative to the light axis of the second light source, the first light source is disposed in the vehicle on a right front pillar, the second light source is disposed in the vehicle on a surface of a ceiling of the vehicle at a proximity of a foot of a rearview mirror post.

19. The installation method of claim 18, wherein a steering wheel is disposed on a right side in a vehicle body.

20. The installation method of claim 18, wherein the positional relationship between the first light source and the second light source is changed in a right-left symmetrical manner when a steering wheel is disposed on a left side in a vehicle body.

21. The installation method of claim 18, wherein the control unit executes a control based on the driver's eye image imaged by the camera and executes an operation for driver's condition determination.

22. An installation method of an eye condition detection apparatus that includes a first light source, a second light source, a camera for imaging a driver's eye image in a vehicle under a light from the first and the second light sources, and a control unit for executing a control based on a condition of the driver's eye image imaged by the camera, the installation method comprising:

positioning the camera in a front direction relative to a driver's seat in the vehicle;

positioning the first light source in a front part of the driver's seat in a front portion of the vehicle with a rightward position shift by at least 20 centimeters from the camera; wherein the second light source is positioned at the front part of the driver's seat in the front portion of the vehicle with a leftward position shift by at least 20 centimeters from the camera, the first light source and the second light source are positioned apart from each other by at least 20 centimeters in the vertical direction of the vehicle, the first light source is disposed in the vehicle on a right front pillar, and the second light source is disposed in the vehicle on a surface of a ceiling of the vehicle at a proximity of a foot of a rearview mirror post.

23. An installation method of an eye condition detection apparatus that includes a first light source, a second light source, a camera for imaging a driver's eye image in a vehicle under a light from the first and the second light sources, and a control unit for executing a control based on a condition of the driver's eye image imaged by the camera, the installation method comprising:

positioning the first light source on a right side relative to a head of a driver in a driver's seat with a tilt angle of at least 15 degrees relative to a front direction of the driver; and positioning the second light source on a left side relative to the head of the driver in the driver's seat with a tilt angle of at least 15 degrees relative to the front direction of the driver, wherein a direction from the head of the driver to the first light source and a direction from the head of the driver to the second light source make an angle of at least 15 degrees in the vertical direction of the vehicle, the first light source is disposed in the vehicle on a right front pillar, and the second light source is disposed in the vehicle on a surface of a ceiling of the vehicle at a proximity of a foot of a rearview mirror post.

24. An installation method of an eye condition detection apparatus that includes a first light source, a second light source, a camera for imaging a driver's eye image in a vehicle under a light from the first and the second light sources, and a control unit for executing a control based on a condition of the driver's eye image imaged by the camera, the installation method comprising:

- positioning the camera on one of an outside of a steering column case and an inside of a meter panel of the vehicle;
- positioning the first light source in the vehicle on a right front pillar, and
- positioning the second light source in the vehicle on a surface of a ceiling of the vehicle at a proximity of a foot of a rearview mirror post.

25. An installation method of an eye condition detection apparatus that includes a first light source, a second light source, a camera for imaging a driver's eye image in a vehicle under a light from the first and the second light sources, and a control unit for executing a control based on a condition of the driver's eye image imaged by the camera, the installation method comprising:

- positioning the camera on one of an outside of a steering column case, an inside of a meter panel and an outside of the dashboard structure in front of the driver of the vehicle;
- positioning the first light source in the vehicle on a right front pillar, and
- positioning the second light source in the vehicle on a surface of a ceiling at a proximity of a foot of a rearview mirror post.

* * * * *